United States Patent [19]
Hong et al.

[11] Patent Number: 6,015,338
[45] Date of Patent: Jan. 18, 2000

[54] ABRASIVE TOOL FOR GRINDING NEEDLES

[75] Inventors: Keith C. Hong, Brookline; Patrick E. Dwyer, Shrewsbury; Elinor B. Keil, Worcester; Edward Lambert, Westboro; Fershid Aspi, Boston, all of Mass.

[73] Assignee: Norton Company, Worcester, Mass.

[21] Appl. No.: 08/919,871

[22] Filed: Aug. 28, 1997

[51] Int. Cl.[7] .................................................. B24D 3/28
[52] U.S. Cl. ......................... 451/541; 451/309; 451/298
[58] Field of Search .............................. 451/541; 51/298, 51/309, 300

[56] References Cited

U.S. PATENT DOCUMENTS

| | | | |
|---|---|---|---|
| 3,594,296 | 7/1971 | Derwall | 204/200 |
| 3,661,544 | 5/1972 | Whitaker | 51/295 |
| 3,864,101 | 2/1975 | Charvat | 51/298 |
| 3,975,864 | 8/1976 | Glowacki | 51/165.87 |
| 4,104,833 | 8/1978 | Glowacki | 51/281 |
| 4,384,942 | 5/1983 | Glowacki | 204/129.46 |
| 5,104,424 | 4/1992 | Hickory et al. | 51/309 |
| 5,263,974 | 11/1993 | Matsutani et al. | 606/223 |
| 5,366,524 | 11/1994 | Holcombe, Jr. et al. | 51/293 |
| 5,575,780 | 11/1996 | Saito | 604/272 |
| 5,630,268 | 5/1997 | Smith et al. | 29/557 |
| 5,644,834 | 7/1997 | Smith et al. | 29/557 |
| 5,658,194 | 8/1997 | Micheletti | 451/541 |

FOREIGN PATENT DOCUMENTS

| | | | |
|---|---|---|---|
| 2330504 | 11/1975 | France | B24D 003/34 |
| 1170848 | 11/1969 | United Kingdom | B23P 1/02 |

*Primary Examiner*—Robert A. Rose
*Attorney, Agent, or Firm*—Mary E. Porter

[57] ABSTRACT

Abrasive tools and a grinding process are for use in the manufacture of hypodermic needles. In particular, a formulation including selected bond components, and a process for manufacturing grinding wheels having an embrittled bond permits a new method for grinding of fine hollow metal tubes to shape the tips of hypodermic needles with the substantial elimination of metal burrs or fines from the grinding process.

11 Claims, 1 Drawing Sheet

ABRASIVE TOOL FOR GRINDING NEEDLES

BACKGROUND

A hypodermic needle contains a hollow metal tube having a lumen opening extending in an nominal diagonal line across the distal end of the tube. The opening comes to a tapered point or lancet at the tip of the needle and the walls of the tube present a beveled face. The tapered, diagonal opening and beveled face facilitate skin puncture and delivery of the therapeutic agent by the tip of the needle.

In most hypodermic needle manufacturing operations, one or more grinding steps are used to shape the needle tip. Needle grinding methods include processes for grinding single needles and, more often, magazines or assemblies containing a plurality of needles in a parallel array. Traverse grinding and/or oscillating plunge grinding processes are used most frequently. Automated operations for continuous production of needles have been described. See, for example, U.S. Pat. Nos. 4,104,833, 4,384,942 and 5,575,780, which are hereby incorporated by reference. One persistent problem encountered in needle grinding operations is the formation of burrs and metal fines on the needle tips.

The presence of metal burrs, fines or slivers on the needle tips may create pain or other adverse consequences during use. Grinding processes used in needle manufacturing commonly produce burrs and fines. To avoid burr formation and to create the sharp, precise beveled face of the needles, typical grinding wheels used commercially in needle finishing must be dressed at frequent intervals. Frequent dressing causes a loss of grinding wheel life and increases the cost of the manufacturing operation. In some operations, the needles also are polished, cleaned with electrolytic treatment (see, e.g., GB-B-1,170,848) or otherwise further processed after grinding to insure removal of such debris. Such additional processing steps represent an undesirable manufacturing expense and complication.

In the alternative, burrs have been eliminated or substantially reduced by using a very soft bond (e.g., an alkyd polyester resin bond, or a shellac bond), but such wheels have an unacceptably short grinding life and are not commercially viable solutions to the problem of burrs. Fillers having a lamellar structure, such as graphite, molybdenum disulfide and hexagonal boron nitride, are suggested in FR-A-2,330,504 as additives for use at 30 to 130 volume percent of abrasive grain to improve abrasive grinding wheel designed for lapping, polishing and grinding hypodermic needles.

The problems of the prior art are avoided to a significant degree by utilizing the abrasive tools and grinding process of the invention. In particular, the inventive formulation and process for manufacturing self-dressing grinding wheels permits the grinding of fine hollow metal tubes (cannula) to form the tapered tips on hypodermic needles without leaving burrs or metal fines on the needle tips.

The abrasive tools of the invention are "self-dressing" in the sense that the tool structure permits bond fracture to occur at an optimum rate, i.e., faster than prior art bonds, but not so fast as to shorten tool life beyond an economically acceptable amount. The tool structure allows coolant flow at the grinding face and removal of grinding debris before the debris loads the grinding face of the tool, necessitating dressing of the tool face. Depending upon the particular grinding process and the particular workpiece, dressing may be eliminated completely or the number of dressing cycles over the life of the wheel may be substantially reduced by utilizing the self-dressing tools of the invention which do not load with metal fines during the grinding operation.

The tools of the invention also cause less workpiece burn and draw less power during grinding than the tools used in the past because the grinding face of the tools of the invention tend not to load with metal fines.

While the tools of the invention are particularly useful in the needle tip grinding method of the invention, their bond system, grain content and balanced friability/strength functional properties make these abrasive tools suitable for similar grinding operations. such operations include the grinding of suture needle tips, lanceted surgical or medical devices or tools and other medical devices such as trocars. These devices and tools all have precise geometric shapes and rigid specifications for control of metal fines or burrs.

SUMMARY OF THE INVENTION

The invention is a self-dressing abrasive tool for grinding needle tips, comprising phenolic resin, 240 to 800 grit abrasive grain, hollow ceramic spheres, and powdered filler, wherein the abrasive tool is manufactured by a process comprising the steps:

a) blending the phenolic resin, abrasive grain, hollow ceramic spheres and powdered filler to form a mixture;

b) pressing the mixture in a mold to form an uncured abrasive tool;

c) heating the uncured abrasive tool to about 155 to 165° C. and holding the uncured abrasive tool at 155 to 165° C. for 6 to 12 hours to form an intermediate bonded abrasive tool; and d) heating the intermediate bonded abrasive tool to a maximum temperature of at least 175° C. and holding the abrasive tool at maximum temperature for 6 to 12 hours to embrittle the bond and form the abrasive tool; and wherein the abrasive tool effectively grinds cannula to form needle tips which are substantially free of burrs.

The invention also provides a self-dressing abrasive tool for grinding needle tips without forming burrs, comprising 15 to 25 volume percent long flow phenolic resin, 36 to 48 volume percent abrasive grain, 3 to 10 volume percent hollow glass/ceramic spheres, and 0.5 to 3.5 volume percent powdered filler. The filler is preferably calcium fluoride powder.

The invention additionally provides a method for grinding needle tips, comprising the steps:

a) providing an abrasive wheel having a grinding face, and comprising a bond consisting of long flow phenolic resin and powdered filler, abrasive grain having a grit size of about 6 to 44 microns and hollow ceramic spheres;

b) mounting the abrasive wheel on a grinding machine adapted for grinding needles;

c) rotating the abrasive wheel at a speed up to a maximum speed of 48.5 m/sec (9500 sfpm) with a coolant flow directed to at least one point along the grinding face of the abrasive wheel; and d) contacting the abrasive wheel with an end of a cannula for a time and at a pressure effective to remove metal and grind a geometric shape into the end of the cannula; whereby the abrasive wheel removes metal fines and debris from the end of the cannula during grinding and the bond fractures at a rate effective to substantially eliminate formation of metal burrs on the needle tips.

DESCRIPTION OF THE PREFERRED EMBODIMENTS

Figure 1:
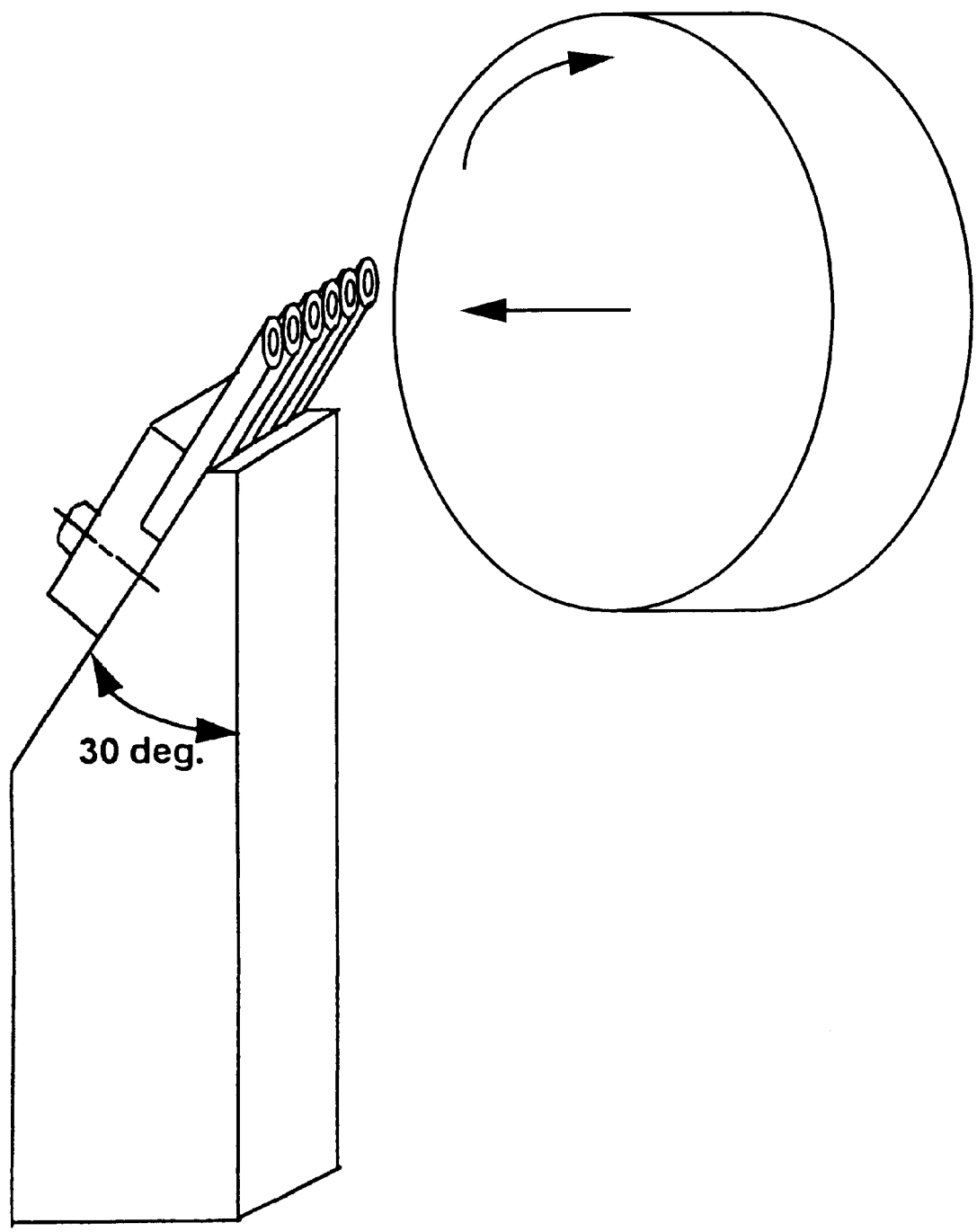
FIG. 1 is a planar view illustrating the orientation of a grinding wheel with respect to an assembly of needles and showing the shape of the needle tip resulting from an initial grinding step.

The abrasive tools of the invention are resin bonded wheels containing about 15 to 25 volume % bond, 36 to 48 volume % microabrasive grain, 3 to 10 volume % hollow ceramic spheres and 0.5 to 3.5 volume % powdered filler. As used herein, "microabrasive" refers to abrasive grains having a FEPA grit size of about 240 to 800 (6 to 44 microns).

The preferred abrasive grain is silicon carbide grain and grain blends comprising at least 90 volume % silicon carbide grain. Suitable grain may be obtained from Saint-Gobain Industrial Ceramics, Worcester, Mass., under the Crystolon® name as either green or black grain. Preferred grit sizes are about 240 to 800, and most preferred grit sizes are about 400 to 600 grit (8 to 18 microns). On a total grain volume basis, the silicon carbide grain may be blended with up to 10 volume % of other microabrasive grains. Suitable secondary grains include, but are not limited to, fused aluminum oxide, sintered sol gel aluminum oxide comprising microcrystalline alpha-alumina, aluminum zirconium (Norzon® grain), diamond and cubic boron nitride, and mixtures thereof.

Suitable hollow ceramic spheres include bubble mullite, bubble alumina and glass spheres, and mixtures thereof, having a particle size of about 10 to 150 microns. As used herein, "hollow ceramic spheres" refers to hollow spheres having walls consisting of ceramic material or consisting of a combination of glass and ceramic material, such as the silica-alumina spheres available commercially as Z-Light® spheres from Zeeland Industries. Preferred for use herein are glass/ceramic spheres having a bulk density of about 0.77 g/cc (helium pycnometry CHM-CHR-0200), a loose packed density of about 0.36 to 0.42 g/cc (ASTM B74.4-1977) and a wall density of about 2.45 g/cc, with an average wall thickness of about 4 to 6 microns and about 69% porosity.

The resin used to form the bond comprises a thermosetting, long flow, phenolic resin powder and about 6 to 16 wt. %, preferably 6 to 7 wt. %, of a cross-linking agent, such as hexamethylenetetramine. As used herein, "long flow" refers to low viscosity resins having a DIN ISO 8619 flow length at 125° C. of about 2–3 times the flow length of phenolic resins typically used in resin bonded abrasive wheels. Flow lengths of about 95 to 145 mm are preferred. A suitable Bis-phenol-A modified resin, designated Durite® AD-885A phenolic resin, may be obtained from Borden, Inc., Louisville, Ky. It has a DIN ISO 8619 flow length of about 95–105 mm. Unmodified or modified (e.g., epoxy or rubber modified) phenolic resins having short flow (e.g., about 30–60 mm) exhibit poor grain wetting during cure when used with powdered fillers, such as fluorspar, and are not suitable for making the abrasive wheel of the invention.

The fillers are used as a finely divided powder. The fillers are blended with the resin powder and considered to be part of the bond. Unlike the lubricating, laminellar fillers previously used in needle grinding wheels, the fillers useful in the invention do not function as lubricants, and lubricants are not useful fillers. It is believed that the fillers modify the flow of the bond during wetting of the grain, altering the grain/resin interactions and physically modifying the grain/bond interface in the cured wheel. The filler alters the performance of the bond in the cured abrasive wheel so as to optimize bond fracturing during grinding and thereby improve the surface finish of the needle tips without loss of wheel life.

Calcium fluoride (fluorspar) is a preferred filler. Also preferred for use herein are sodium aluminum hexafluoride (cryolite) and potassium aluminum fluoride, and combinations thereof Minor amounts (e.g., up to about 20 vol. % of the total fillers) of other fillers may be used in the filler component of the wheels of the invention. Such fillers include, but are not limited to, iron pyrites, iron sulfide, barium sulfate, potassium fluoroborate, potassium magnesium sulfate, alkali metal chloro ferrate, alkali metal cholorfluoro ferrate, polyvinyl chloride, polyvinylidene chloride, and mixtures thereof.

The abrasive wheels of the invention contain 0.5 to 5 volume % filler, preferably 0.5 to 3.5 volume % filler, most preferably about 1 to 2 volume % filler. Preferred filler material is a powder, having a particulate size of about 200 to 325 US mesh (30 to 60 microns).

The abrasive wheels of the invention may be manufactured by dry blending the components, with the optional addition of wetting agents, such as liquid resole resins, with or without a solvent, such as benzaldehyde, to form an abrasive mixture, cold or hot pressing the mixture in a selected mold to form a green or uncured abrasive tool, and heating the uncured abrasive tool to cure the resin and create an abrasive tool effective for grinding. The mix is typically screened before molding. The mold is preferably constructed of stainless steel or high carbon- or high chrome-steel. Molding is usually done under about 0.5 to 3.0 tsi of pressure (for hot pressing, and up to 10 tsi for cold pressing) for about 30 to 60 seconds for each millimeter of abrasive article thickness (hot pressing) or about 5 to 60 seconds (cold pressing).

The tool preferably is heated to a maximum temperature of about 155 to 165° C. for 6 to 24 hours to crosslink and cure the resin bond. Other similar curing cycles also may be employed. The cured tool is then stripped from the mold and air-cooled. Finishing or edging steps and truing operations to achieve balance may be carried out on the cured tool. Tools manufactured in this curing cycle are preferred for use in grinding larger gauge (1.0 to 1.6 mm) needles. For grinding fine gauge (0.3 to 0.9 mm) needles a more brittle bond is preferred and the multi-step curing process of the invention is used to make the abrasive wheels.

In the manufacturing process of the invention, the curing is carried out in several steps. Initial curing to form an intermediate bonded abrasive tool is carried out at about 155 to 165° C. substantially as described above. The intermediate tool may be cooled to room temperature and held before further processing or immediately subjected to the next curing step. In the subsequent curing step, the intermediate tool is heated to a maximum temperature of at least 175° C. and held at the maximum temperature for about 6 to 12 hours. The maximum temperature preferably does not exceed 200° C. To obtain the preferred bonds, the total curing time is at least 20 hours. At the higher temperatures for long time periods, the bond becomes quite dark and brittle and begins to exhibit too much friability and wheel life suffers. Without the additional process step at higher temperatures, the wheels are more elastic and more likely to load with fines or create burrs on the workpiece.

The most preferred wheels are manufactured with a first curing cycle to about 160° C. for 6 to 12 hours and then a subsequent curing cycle to about 175° C. for about 6 to 12 hours. Also preferred are wheels manufactured with a first curing cycle to about 160° C. for 6 to 12 hours and then a subsequent curing cycle to about 200° C. for about 6 to 12 hours.

By means of resin and filler selections and curing conditions, the resin bond is rendered relatively brittle or friable, and will break or chip faster and the abrasive wheel will have less of a tendency to load with grinding debris than commercially used grinding wheels. Abrasive wheels are dressed with diamond tools and other dressing tools to clear accumulated grinding debris from grinding face. In microabrasive grain wheels, the dressing operation often wears away the wheel faster than the grinding operation. Because the wheel dressing operations are needed less frequently with the resin bonded wheels of the invention, the wheels are consumed more slowly and have a longer wheel life than resin bonded wheels used in the past, including wheels having a stronger, less friable bond. The most preferred wheels have intermediate values for hardness (sand blast penetration), glass transition temperature (Tg), and tan delta (vibration damping properties of the wheel) properties that yield an optimum balance of wheel life with brittleness or tendency of the bond to fracture during grinding.

The wheels made in this way are particularly well suited for grinding hypodermic needle tips without creating metal burrs on the needle tips. A preferred grinding process comprises the steps of mounting the abrasive wheel of the invention on a grinding machine adapted for grinding needles, rotating the abrasive wheel at a speed up to a maximum speed of 48.5 m/sec (9500 sfpm) with a coolant flow directed to the grinding face of the abrasive wheel, and contacting the abrasive wheel with an end of a cannula for a time and at a pressure effective to remove metal and grind a geometric shape into the end of the cannula. The abrasive wheels of the invention remove metal fines and debris from the end of the cannula during grinding to minimize the number of dressing cycles and substantially eliminate formation of metal burrs on the needle tips.

The cannula may be contained in an assembly adapted for holding a plurality of cannulae in parallel alignment such that metal may be ground from one end of each of the plurality of cannulae in the assembly. A schematic illustration of an assembly is shown in FIG. 1.

For grinding such an assembly of cannulae, the abrasive wheel, or the assembly, or both may be oscillated with respect to each other during grinding and metal is ground simultaneously from the end of each cannula in the assembly in a plunge grinding operation. Here, the wheel width must be equal to or greater than the width of the plurality of cannulae in the assembly. The grinding wheel or the workpiece may be rotated in a direction such that grinding begins at the heel area and ends at the distal area of the needle tips, as shown in FIG. 1.

In an alternative process, the abrasive wheel may sequentially grind metal from successive ends of the plurality of cannulae in the assembly in single or multiple traverse grinding steps.

In a typical process, the end of the cannula is ground to a nominally diagonal primary shape, having an acute angle of about 5 to 40, preferably 7 to 20, degrees in profile. The primary shape comprises in planar view a heel area and a distal area, with the distal area located at the outermost part of the end of the cannula. The end of the cannula is ground in at least one subsequent grinding step to form a lancet in the distal area to sharpen the needle tip. The lancet or additional bevel is at a more acute angle than the primary shape of the needle tip. Following formation of the primary shape, the ends of the cannulae are slightly rotated, a bevel is ground on the exposed edge of the distal area, and the ends of the cannulae are slightly rotated in the opposite direction, and a bevel is ground of the opposite edge of the distal area to complete needle tip formation. In the alternative, the lancet is ground in a single grinding pass over the distal area of the needle. Other grinding processes maybe carried out with the abrasive tools of the invention to create a variety of geometric shapes as desired for particular needle designs.

The following examples illustrate the invention and are not meant to limit the scope of the invention.

EXAMPLE 1

Abrasive grinding wheels (Exp. 1 and control 1, 2, 3 and 4) having the formulations shown in Table 1 were made by blending liquid resin with abrasive grain in a Stephan high shear mixer, mixing for 45 seconds, adding bond (powdered resin, calcium fluoride and bubble mullite) and mixing for 45 seconds to produce 2.72 kg (6 lbs) of abrasive mix. The mix was poured into a mold, cold pressed, and cured by ramping the temperature up to 160° C. over 8 hours, then heating the wheel at 160° C. for 15 hours, and cooling to room temperature (Process 1). Wheels were evaluated for hardness (sand blast penetration, SBP, #2 chamber at 25 psi), dynamic mechanical properties (SEIKO DMS110 module), modulus of elasticity or MOE (J.W.Lemmens MK5 Industrial Grindosonic) and flexural strength (ASTM D790-91). Results are shown in Table 2.

TABLE 1

| | Abrasive Wheel Formulation Wt. % (Vol. %) | | | | |
|---|---|---|---|---|---|
| Sample | Abrasive SiC | Abrasive Al$_2$O$_3$ | Resin | Fluorspar | Bubble Mullite |
| control 1 | 77.86 (38.00) | none | 18.44 (22.50) | none | 3.70 (7.50) |
| Exp. 1 | 78.22 (40.00) | none | 16.43 (21.00) | 2.72 (1.40) | 2.63 (5.60) |
| control 2 | 77.41 (42.00) | none | 10.84 (13.83) | 6.87 (3.45) | 4.92 (10.37) |
| control 3 | 76.73 (38.00) | none | 21.81 (27.00) | none | 1.46 (3.00) |
| control 4 | 79.02 (38.00) | none | 14.97 (18.00) | none | 6.00 (12.00) |
| Exp. 2 | 78.22 (40.00) | none | 16.43 (21.00) | 2.72 (1.40) | 2.63 (5.60) |
| Exp. 3 | 78.22 (40.00) | none | 16.43 (21.00) | 2.72 (1.40) | 2.63 (5.60) |
| control 5 | 69.13 (36.00) | 9.48 (4.00) | 16.13 (21.00) | 2.67 (1.40) | 2.59 (5.60) |
| control 6 | 51.90 (28.00) | 27.46 (12.00) | 15.57 (21.00) | 2.58 (1.40) | 2.50 (5.60) |

*Abrasive grain was 500 grit Crystolon ® silicon carbide grain or 500 grit aluminum oxide grain obtained from Saint-Gobain Industrial Ceramics, Worcester, MA. Black silicon carbide was used in controls 1–4. A 400/500 grit mixture of green silicon carbide grain was used in samples Exp. 1–3 and controls 5 & 6.
*Resin was Durite ® AD-886A phenolic resin powder obtained from Borden, Inc., having a DIN ISO 8619 flow length of 99 mm.
*Bubble mullite was Z-light W1000 spheres (10 to 150 micron size) obtained from Zeelan Industries.
*Fluorspar (calcium fluoride) was obtained from Aldrich Chemical Co.

TABLE 2

| | Wheel Properties | | | | |
|---|---|---|---|---|---|
| Sample | Cured Density g/cc | SBP 2 @ 25 mm | MOE (dy/cm2) × 10$\wedge$10 | Dynamic Mechanical Analysis (@ 1 Hz, 3-point bending mode) Tg °C. | tan delta |
| control 1 | 1.54 | 0.86 | 14.3 | 202 | 0.48 |
| Exp. 1 | 1.61 | 0.78 | 13.8 | 193 | 0.53 |

TABLE 2-continued

Wheel Properties

| Sample | Cured Density g/cc | SBP 2 @ 25 mm | MOE (dy/cm2) × 10^10 | Dynamic Mechanical Analysis (@ 1 Hz, 3-point bending mode) Tg °C. | tan delta |
|---|---|---|---|---|---|
| control 2 | 1.62 | 2.87 | 15.4 | 225 | 0.28 |
| control 3 | 1.59 | 0.42 | 14.6 | 200 | 0.43 |
| control 4 | 1.52 | 1.60 | 13.9 | 201 | 0.44 |

Grinding tests were conducted with wheels listed in Table 1 and a wheel used commercially in needle grinding operations (Control A). The control wheel contained about 24% resin bond (epoxy modified phenolic resin), 44% silicon carbide abrasive grain (about 500 grit size) and about 32% porosity, on a volume basis, with no filler material.

Grinding tests utilized the following test conditions:
Machine: Meyer Burger TS121 CNC Slicing Machine
Workpiece: An assembly of 6 #16RW gage, 304 SS needles were mounted in a manual fixture, at a 30° angle as shown in FIG. 1. The nominal needle dimensions were 0.0655 inch (1.66 mm) O.D.×0.0485 inch (1.23 mm) I.D.×1.25 inch (31.75 mm) long.
Grinding Wheels: 4 inches (100 mm) diameter by 0.50 (12.5 mm) wide. Wheel speed was 6500 SFM (33 m/s). The wheel rotation direction was from the heel of the needle to the tip.
In-Feed: Each wheel was tested using 1 magazine load of needles for each of three in-feed rates; 0.30 in/min (7.62 mm/min), 0.60 in/min (15.24 mm/min), and 1.00 in/min (25.4 mm/min). At each plunge rate an infeed amount of 0.100 inch (2.54 mm) was performed 4 times with the wheel centerline maintained on the centerline of the needle face. Between each plunge the needles were manually indexed toward the wheel, along the 30° fixture face, by 0.200 inches (5.93 mm).
Dressing: Following the initial wheel truing, a conditioning grind was performed to form the 30° profile onto the needle. After conditioning, the wheel was again trued using a single point diamond, at 0.001 in. (0.025 mm) radial compensation and 10 in/min (250 mm/min) dress speed. No further truing was performed.
Coolant: Master Chemical Trim SC210 semisynthetic coolant was used at 5% in water.

Following grinding, visual evaluations of the needle quality (e.g. degree of slivers, burrs, burns, etc. without an air blasting cleaning step) were recorded. Needle tip quality was judged acceptable in those samples having a minor amount of burrs or fines of the type easily removed in an air cleaning operation.

TABLE 3

Grinding Test Results

| Sample | MRR (in.3/min) | Power (kw) | G-Ratio | Burrs/Fines |
|---|---|---|---|---|
| control 1 | 0.01799 | 0.644 | 0.124 | burrs, long heavy fines |
| Exp. 1 | 0.01745 | 0.585 | 0.253 | acceptable |
| control 2 | 0.01378 | 0.365 | 0.088 | none |
| control 3 | 0.01754 | 0.756 | 0.140 | long fines |
| control 4 | 0.01264 | 0.573 | 0.086 | acceptable |
| Exp. 3 | 0.01804 | 0.420 | 0.295 | acceptable |
| Exp. 2 | 0.01797 | 0.450 | 0.226 | acceptable |
| control 5 | 0.01800 | 0.499 | 0.249 | small fines |
| control 6 | 0.01798 | 0.615 | 0.233 | medium fines |
| control A | 0.01758 | 0.629 | 0.293 | medium fines |

The grinding test showed the best grindability and the best workpiece finish were obtained with wheels of the invention containing silicon carbide microabrasive grain, 1.4 vol. % calcium fluoride, and 5.6 vol.% bubble mullite in long flow phenolic resin (Exp. 1–3). Aluminum oxide grain blends (controls 5 & 6) drew too much power and wheels containing more than 6 vol. % of spheres or more than 2 vol. % of filler were too soft and/or metal removal rates were too low (controls 1, 2 & 4).

Excessive burrs were observed following grinding with a higher percentage of aluminum oxide grain, and with excessive amount of hollow ceramic spheres, and in the absence of calcium fluoride filler (controls 1, 2, 4, 5, 6 and A).

It can be inferred from measuring the reduced grinding power and, in some cases, equal or greater G-ratios at equivalent MRRs and by visually observing and comparing the amount of burrs and fines on the needle tips after grinding that the experimental wheels would allow a longer dress interval. That is, these wheels are self-dressing and would grind longer than commercially used abrasive wheels having different bond systems before the need for re-sharpening and removal of debris from the grinding face would be necessary.

EXAMPLE 2

An abrasive wheel (Exp. 1 of Table 1) was made utilizing Process 1 of Example 1 and compared to wheels made utilizing either Process 2 or Process 3, described below. These wheels, Exp. 1, Exp. 2 and Exp. 3, contained the following mix components mixed in 2.72 kg (6 lbs) quantities as described in Example 1. Process 3 also was used to make additional wheels, control 5 and control 6 having the formulations shown in Table 1. Results of wheel evaluations and a comparison with control wheels used commercially in needle grinding operations are shown in Table 4, below.

| Abrasive Wheel Mix Components: | |
|---|---|
| Component | Wt. % |
| Silicon carbide grain (50/50 mix of 500/400 grit 39C) | 78.22 |
| Resin | 16.43 |
| CaF2 | 2.72 |
| Bubble mullite | 2.63 |
| | 100.00 |

Process 2: The molded wheels were cured by Process 1, cooled to room temperature and then ramped up to 175° C. over 9 hours, and heated at 175° C. for 18 hours, followed by cooling to room temperature.

Process 3: The molded wheels were cured by Process 1, cooled to room temperature and then ramped up to 175° C. over 3 hours, ramped up to 200° C. over 1 hour, heated at 200° C. for 19 hours and cooled to room temperature.

TABLE 4

Wheel Properties

| Sample | Cured Density g/cc | SBP 2 @ 25 mm | MOE (dy/cm2) × 10^10 | Dynamic Mechanical Analysis (@ 1 Hz, 3-point bending mode) Tg °C. | tan delta |
|---|---|---|---|---|---|
| controls | | | | | |
| control C | 1.72 | 1.00 | — | 252 | 0.27 |
| control A | 1.55 | 0.32 | — | 266 | 0.07 |
| control B | 1.70 | 0.54 | — | 180 | 0.26 |
| process 1 | | | | | |
| Exp. 1 process 2 | 1.61 | 0.78 | 13.8 | 193 | 0.53 |
| Exp. 2 process 3 | 1.61 | 0.93 | 14.1 | 228 | 0.27 |
| Exp. 3 | 1.60 | 1.44 | 14.4 | 242 | 0.15 |
| control 5 | 1.64 | 1.48 | 14.5 | — | — |
| control 6 | 1.69 | 1.59 | 14.2 | — | — |

Control wheel A contained about 24% resin bond (epoxy modified phenolic resin), 44% silicon carbide abrasive grain (about 500 grit size) and about 32% porosity, on a volume basis, with no filler material. Control wheel B contained about 27% resin bond (epoxy modified phenolic resin), 38% silicon carbide abrasive grain (about 500 grit size) and about 35% porosity, on a volume basis, with no filler material. Control wheel C contained about 28% resin bond (nitrile rubber modified phenolic resin with a flow length of 36–46 mm ), 40% silicon carbide abrasive grain (about 500 grit size) and about 32% porosity, on a volume basis, with no filler material.

Wheel segments were measured for flexural strength and all wheels made by the experimental processes of the invention were found to be equivalent to control wheels used commercially in needle grinding operations.

The wheels were tested in commercial needle grinding operations. The process 1 wheel had 160% longer wheel life than commercial control C in grinding larger gauge (1.69 mm O.D.) needles, and the process 2 wheel had 200% longer wheel life relative to control C in smaller gauge (0.83 mm O.D.) needles. The longer wheel life was achieved, at least in part, because over time the tested wheels produced less surface damage (burrs/fines) on the ground needles thereby allowing the dressing intervals to be increased by 100% to 150% over the control wheels.

We claim:

1. A self-dressing abrasive tool comprising phenolic resin, 240 to 800 grit abrasive grain, hollow ceramic spheres, and powdered filler, wherein the abrasive tool is manufactured by a process comprising the steps:
   a) blending the phenolic resin, the abrasive grain, hollow ceramic spheres and the powdered filler to form a mixture;
   b) pressing the mixture in a mold to form an uncured abrasive tool;
   c) heating the uncured abrasive tool to about 155 to 165° C. and holding the uncured abrasive tool at 155 to 165° C. for 6 to 12 hours to form an intermediate bonded abrasive tool; and
   d) heating the intermediate bonded abrasive tool to a maximum temperature of at least 175° C. and holding the abrasive tool at maximum temperature for 6 to 12 hours to embrittle the bond and form the abrasive tool, and wherein the abrasive tool effectively grinds cannulae to form needle tips which are substantially free of burrs.

2. The abrasive tool of claim 1, wherein the intermediate bonded abrasive tool is heated to a maximum temperature of about 175 to 200° C.

3. The abrasive tool of claim 1, wherein the phenolic resin is a long flow resin having a DIN ISO 8619 flow length of at least 95 mm.

4. The abrasive tool of claim 1, wherein the phenolic resin is a long flow resin having a DIN ISO 8619 flow length of 95 to 145 mm.

5. The abrasive tool of claim 1, wherein about 6 to 7 wt. % of hexamethylenetetramine is added to the phenolic resin as a crosslinking agent.

6. The abrasive tool of claim 1, wherein the abrasive grain is selected from the group consisting of silicon carbide grain, and mixtures of grain containing at least 90 vol. % silicon carbide grain.

7. The abrasive tool of claim 1, wherein the hollow ceramic spheres are selected from the group consisting of bubble mullite, spheres consisting of a combination of glass and ceramic material, glass spheres and bubble alumina, and combinations thereof.

8. The abrasive tool of claim 7, wherein the hollow ceramic spheres are spheres consisting of a combination of glass and ceramic material and having a size of about 10 to 150 microns.

9. The abrasive tool of claim 1, wherein the powdered filler is selected from the group consisting of calcium fluoride, sodium aluminum hexafluoride and potassium aluminum fluoride, and combinations thereof.

10. The abrasive tool of claim 3, wherein the abrasive tool comprises 15 to 25 volume percent long flow phenolic resin, 36 to 48 volume percent abrasive grain, 3 to 10 volume percent hollow ceramic spheres, and 0.5 to 3.5 volume percent powdered filler.

11. An abrasive tool comprising 15 to 25 volume percent phenolic resin having a flow length of at least 95 mm according to DIN ISO 8619 test method, 36 to 48 volume percent silicon carbide abrasive grain having a grit size of about 6 to 44 microns, 3 to 10 volume percent hollow spheres consisting of a combination of glass and ceramic material, and 0.5 to 3.5 volume percent powdered filler, the filler being selected from the group consisting of calcium fluoride, sodium aluminum hexafluoride and potassium aluminum fluoride, and combinations thereof.

* * * * *